(12) United States Patent
Levine et al.

(10) Patent No.: US 11,380,230 B2
(45) Date of Patent: Jul. 5, 2022

(54) POINT OF USE INTERACTION PLAYBACK DEVICE EMPLOYING ENERGY HARVESTING FROM AMBIENT RADIO FREQUENCY COMMUNICATIONS

(71) Applicant: Becton, Dickinson and Company, Franklin Lakes, NJ (US)

(72) Inventors: Claire Letito Levine, Wayne, NJ (US); Mojtaba Kashef, Boxford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1 day.

(21) Appl. No.: 15/772,202

(22) PCT Filed: Nov. 8, 2016

(86) PCT No.: PCT/US2016/060915
§ 371 (c)(1),
(2) Date: Apr. 30, 2018

(87) PCT Pub. No.: WO2017/083262
PCT Pub. Date: May 18, 2017

(65) Prior Publication Data
US 2018/0315360 A1    Nov. 1, 2018

Related U.S. Application Data

(60) Provisional application No. 62/252,881, filed on Nov. 9, 2015.

(51) Int. Cl.
*G09G 1/00*      (2006.01)
*G02F 1/153*     (2006.01)
(Continued)

(52) U.S. Cl.
CPC ........... *G09G 1/005* (2013.01); *G02F 1/1533* (2013.01); *G06F 3/14* (2013.01); *G06F 3/147* (2013.01);
(Continued)

(58) Field of Classification Search
CPC combination set(s) only.
See application file for complete search history.

(56) References Cited

U.S. PATENT DOCUMENTS

| 5,232,388 A | 8/1993 | Danjell |
| 6,348,908 B1 | 2/2002 | Richley et al. |

(Continued)

FOREIGN PATENT DOCUMENTS

| CN | 103812226 A | 5/2014 |
| CN | 104753182 A | 7/2015 |

(Continued)

OTHER PUBLICATIONS

International Search Report dated Jan. 30, 2017, which issued in Application No. PCT/US2016/060915, 3 pages.

(Continued)

*Primary Examiner* — Deeprose Subedi
(74) *Attorney, Agent, or Firm* — Dickinson Wright PLLC

(57) ABSTRACT

Devices, systems and methods are provided for playing back video or other dynamic content at a point of interaction with one or more users via a device that is configured on a sticker, label, card or other substrate. The device is self-powered and employs ambient radio frequency energy harvesting to charge a renewable, rechargeable energy storage element. The device has a display for displaying static content until dynamic content such as the video content is output in response to a user input. The display on the device can be used for outputting the video content, or the device can transmit the video content to an NFC-enabled smart phone (Continued)

for display without the smart phone having to download the video content from the internet.

20 Claims, 6 Drawing Sheets

(51) Int. Cl.
  *G06F 3/147* (2006.01)
  *H02J 50/20* (2016.01)
  *H02J 50/30* (2016.01)
  *A61M 16/10* (2006.01)
  *G06F 3/14* (2006.01)
  *A61M 5/315* (2006.01)

(52) U.S. Cl.
  CPC .............. *H02J 50/20* (2016.02); *H02J 50/30* (2016.02); *A61M 5/31548* (2013.01); *A61M 2205/33* (2013.01); *A61M 2205/3576* (2013.01); *A61M 2205/502* (2013.01); *A61M 2205/52* (2013.01); *G09G 2330/02* (2013.01); *G09G 2370/22* (2013.01); *G09G 2380/04* (2013.01)

(56) References Cited

U.S. PATENT DOCUMENTS

| | | | |
|---|---|---|---|
| 2009/0006720 | A1 | 3/2009 | Martin et al. |
| 2009/0067208 | A1* | 3/2009 | Martin ............... H02J 7/025 363/126 |
| 2010/0011639 | A1 | 1/2010 | Goode et al. |
| 2011/0102304 | A1 | 5/2011 | Nelson |
| 2012/0194448 | A1* | 8/2012 | Roth ..................... G06F 1/1616 345/173 |
| 2012/0220224 | A1 | 8/2012 | Walker |
| 2014/0001534 | A1 | 1/2014 | Mohamadi |
| 2014/0015344 | A1 | 1/2014 | Mohamadi |
| 2015/0110476 | A1* | 4/2015 | Walker ............... G06Q 30/0272 386/359 |
| 2017/0104425 | A1* | 4/2017 | Meloche ............ A61B 5/14542 |
| 2018/0255350 | A1* | 9/2018 | Rumreich .......... H04N 21/4345 |

FOREIGN PATENT DOCUMENTS

| | | |
|---|---|---|
| CN | 104795906 A | 7/2015 |
| JP | 2012-517796 A | 8/2012 |
| JP | 2013-20059 A | 1/2013 |
| JP | 2013-50565 A | 3/2013 |
| JP | 2014-512552 A | 5/2014 |
| JP | 2015-46861 A | 3/2015 |
| JP | 2015-187724 A | 10/2015 |
| WO | WO 2014/137374 A1 | 9/2014 |

OTHER PUBLICATIONS

Japanese Office Action dated Oct. 6, 2020, which issued in the corresponding Japanese Patent Application No. 2018-523509, including English translation.

Chinese Office Action dated Sep. 11, 2020, which issued in the corresponding Patent Application No. 201611272548.7, including English translation.

* cited by examiner

POINT OF USE INTERACTION PLAYBACK DEVICE EMPLOYING ENERGY HARVESTING FROM AMBIENT RADIO FREQUENCY COMMUNICATIONS

BACKGROUND OF THE INVENTION

Field of the Invention

The present invention relates to systems, methods and apparatuses for generating viewable content (e.g., static content such as graphic display or dynamic content such video) by a self-powered device at a point of interaction with one or more users that employs ambient radio frequency energy harvesting to charge a renewable, rechargeable energy storage element.

Description of Related Art

It has been cost prohibitive for companies, manufacturers, and individuals, among other entities, to deliver a video demonstration of a product or an idea to other individuals at a point of display such as at a retail point of display or sale (e.g., a store shelf), in a healthcare setting/clinic, in the home, at a trade show or any other location, without the use of a display device such as a battery operated screen, TV monitor, computer, iPad or similar portable computer, or smart phone, and a power source connection for powering or recharging the display device.

A need exists for a point of user interaction device and method of using same that provides static or dynamic content and is self-powered (e.g., does not require a connection to an AC or DC power source for powering or recharging, or battery replacement, or other field maintenance by a user).

A need exists for a point of user interaction device and method of using same that provides static or dynamic content and is relatively small in size for convenient display, as well as inexpensive to manufacture and easy to configure with viewable content (e.g., a video segment or static graphical content or a series of static grapgical content or images) for display.

SUMMARY OF THE INVENTION

The above and other problems are overcome, and additional advantages are realized, by illustrative embodiments of the present invention.

It is an aspect of illustrative embodiments of the present invention to provide a device for display of dynamic content at a point of user interaction comprising: a display; a memory device for storing content comprising the dynamic content; a processor configured to controllably output the stored content; and an ambient energy collecting and storage device configured to receive ambient radio frequency energy available at the point of user interaction and charge an energy storage element without use of an external AC or DC power source, the energy storage element being configured to supply power to the display, the memory and the processor being configured to controllably output the stored content.

In accordance with aspects of illustrative embodiments of the present invention, the device comprises a substrate on which the display, the memory device, the processor and the ambient energy collecting and storage device are mounted, the substrate having a top side from which the display is viewable by a user and a bottom side for mounting the substrate at the point of user interaction. For example, the substrate can have dimensions comprising a height in the range of 2"-5" and a length in the range of 4"-7". The substrate can have dimensions comprising a thickness in the range of 0.125"-0.5".

In accordance with aspects of illustrative embodiments of the present invention, the dynamic content is a video segment. For example, the video segment can have a duration in the range of 5 seconds-180 seconds.

In accordance with aspects of illustrative embodiments of the present invention, the processor is configured to playback the dynamic content via the display automatically in response to a user input. For example, the device can comprise a user input device selected from the group consisting of a tactile switch, a touchscreen area on the display, and a user proximity sensor. In addition, the processor can be configured to play the dynamic content one time per user input, for example, or play the dynamic content continuously in a loop, or play the dynamic content periodically.

In accordance with aspects of illustrative embodiments of the present invention, the memory device stores static content, and the processor is configured to display the static content until a user input signal is received and then output the dynamic content in response to the user input signal. For example, the user input signal can be received from a user-activated input device selected from the group consisting of a tactile switch, a touchscreen area on the display, and a user proximity sensor.

In accordance with aspects of illustrative embodiments of the present invention, the processor is configured to transmit the stored dynamic content to a proximal smart mobile device in response to a user input for playback on a display of the smart mobile device. For example, the smart mobile device can be near field communication or NFC-enabled, and the device further comprises a near field communication circuit, and the user input is a user bringing the smart mobile device into proximity with the near field communication circuit of the device. The processor can be configured to transmit the stored dynamic content to the smart mobile device via the near field communication circuit when the near field communication circuit is activated by proximity of the smart mobile device.

Additional and/or other aspects and advantages of the present invention will be set forth in the description that follows, or will be apparent from the description, or may be learned by practice of the invention. The present invention may comprise delivery devices and methods for forming and operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, of which.

Throughout the drawing figures, like reference numbers will be understood to refer to like elements, features and structures.

DETAILED DESCRIPTION OF ILLUSTRATIVE EMBODIMENTS

Figure 1A:
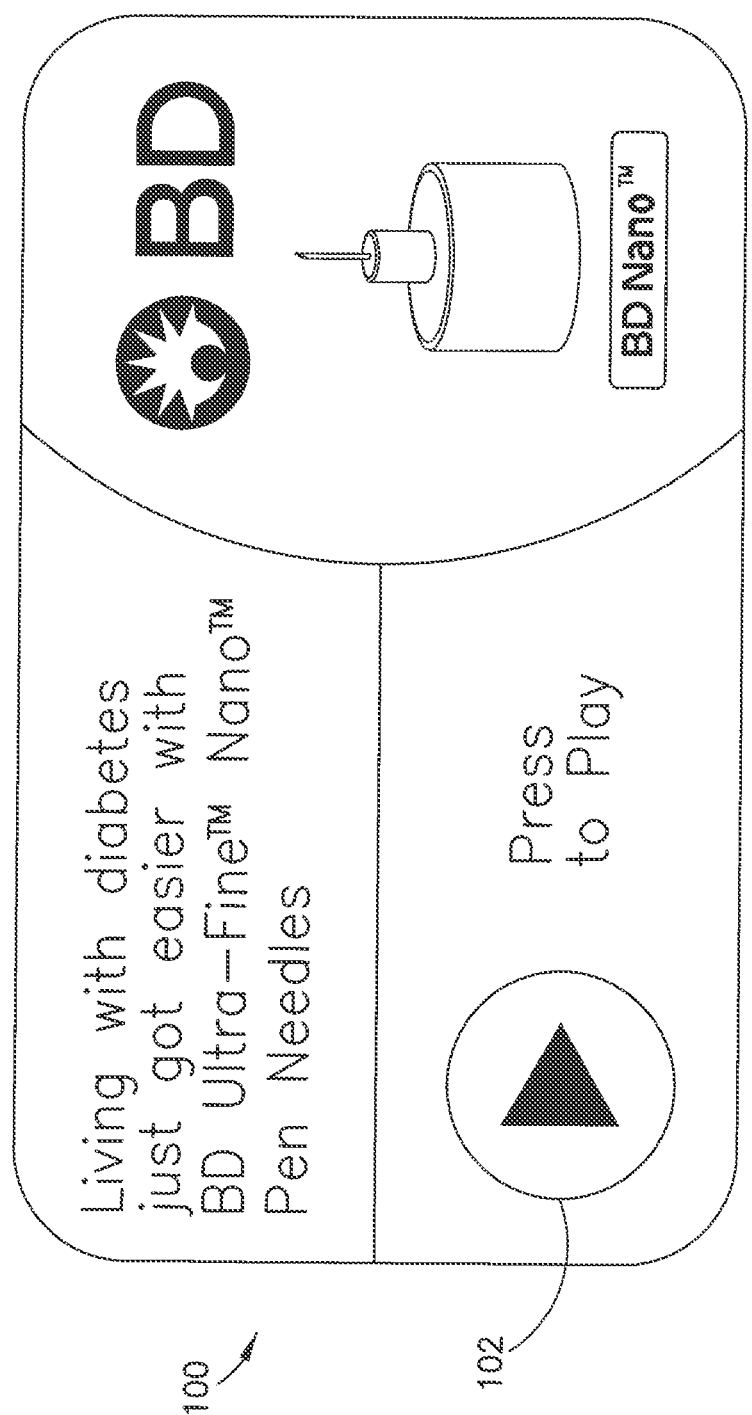
FIGS. 1A and 1B depict a self-powered, point of user interaction device that provides, respectively, viewable static and dynamic content in accordance with an embodiment of the present invention.

Reference will now be made in detail to embodiments of the present invention, which are illustrated in the accompanying drawings. The embodiments described herein exemplify, but do not limit, the present invention by referring to the drawings. As will be understood by one skilled in the art, terms such as up, down, bottom, and top are relative, and are employed to aid illustration, but are not limiting.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

Figure 1B:
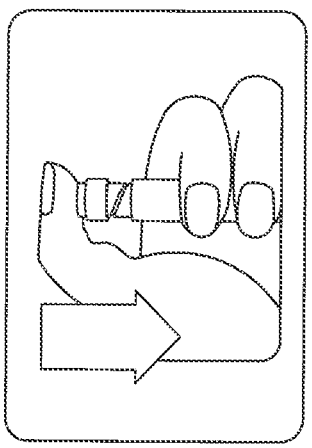

With reference to FIGS. 1A and 1B, a relatively small, thin content display device 100 is provided for displaying or otherwise playing back or outputting static content (e.g., a static image generated on an LED or LCD display) when in a static mode of operation as shown in FIG. 1A, and dynamic content (e.g., a video segment generated on the LED or LCD display) when in a dynamic mode of operation as shown in FIG. 1B. In the illustrated embodiment, the device 100 is, for example, a sticker that is approximately 2 inches by 4 inches in terms of height and width, respectively, and has an area for display or display window of approximately the same dimensions. Any other size of device 100 and corresponding display area can be used (e.g., 4 inches by 6 inches, 5 inches by 7 inches, or other smaller or larger dimensions). The display area shown in FIGS. 1A and 1B is essentially the total front surface area of the device 100. The device 100, however, can be configured to have a smaller display area than its viewable front surface area.

As described below, the device 100 in FIG. 1 is advantageous because video content can be played at a point of user interaction from a sticker 100 or other small display device 100 that has a rechargeable battery or no battery due to harvesting and conditioning of ambient wireless network energy available at the point of user interaction such as a commercial or residential WiFi network (e.g., available in a store or other commercial location, municipal or medical building, residence, and the like) or from the use of Bluetooth™ in a vehicle (e.g., to energize a sticker 100 deployed at a drive-through location or other vehicle-accessible point of advertising or user interaction), and/or ambient light or photovoltaic energy. It is to be understood that the device 100 need not be a sticker with an adhesive, but can be a small display device mounted at the point of user interaction by other means such as a mounting bracket, or via a clip strip on a display shelf, or Velcro fastener. Alternatively, the display 100 can be propped up and freestanding, or applied directly to packaging, or wearable, among other mounting options.

Figure 2:
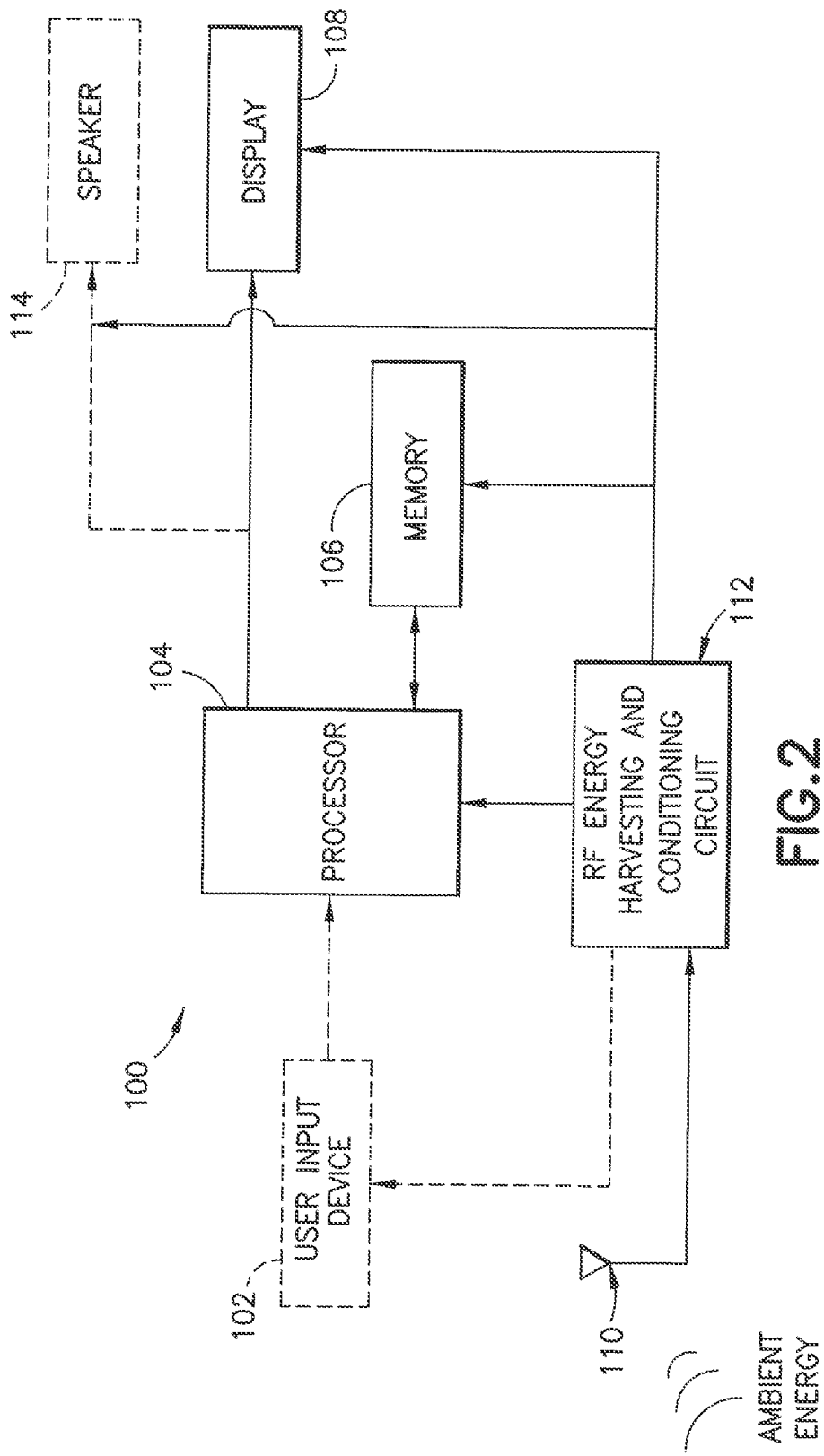
FIG. 2 is a block diagram of components of the device in FIGS. 1A and 1B in accordance with an embodiment of the present invention.

With reference to FIG. 2, the device 100 is provided with, for example, a processor 104, a memory 106 with content to be displayed and optionally code for the processor, a display 108 (e.g., a LED or LCD display or low power display), an optional user input device 102 (e.g., a resistive or capacitive touch sensor that is part of or separate from the display), an optional speaker 114, an antenna 110 or multiple antennae and/or other ambient energy collecting device such as a photovoltaic cell, and an energy harvesting and conditioning circuit 112. The processor 104 can be a programmable processing device such as a microcontroller, microprocessor, a programmable gate array (e.g., FPGA) or application specific integrated circuit (ASIC). The processor 104 and memory 106 can be in the same component or in separate components. The processor 104 can be, for example, a low power microcontroller, or a low power microcontroller or SoC (System-on-Chip) with RF block (e.g., low energy Bluetooth™ (BLE) stack). The device 100 has been described as outputting dynamic content such as video on, for example, an LCD display, when the user input device 102 is activated. The device 100, however, can also be configured to operate using an Electronic Paper Display (EPD) and electrophoretic or electronic ink (E-ink) technology.

Figure 3:
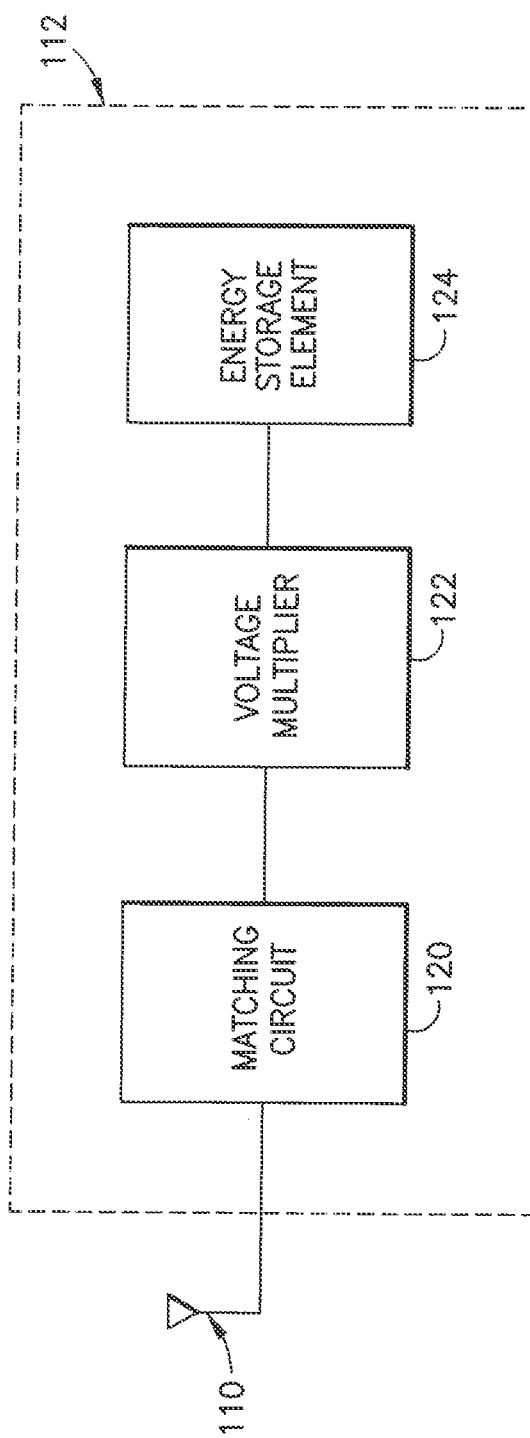
FIG. 3 is a block diagram of the radio frequency (RF) or ambient energy harvesting and conditioning circuit in FIG. 2 in accordance with an embodiment of the present invention.

With reference to FIG. 3, the energy harvesting and conditioning circuit 112 can comprise, for example, a matching circuit 120 for impedance matching with respect to the antenna 110, a voltage multiplier 122 and an energy storage element 124. The energy harvesting and conditioning circuit 112 is configured to receive a selected range or ranges of wireless communication signals corresponding to ambient energy available at the point of user interaction such as near field communication (NFC) frequencies (e.g., 13.56 MHz) or far field communication (FFC) frequencies, or ultra high frequencies (UHF) between 300 MHz and 3 GHz (e.g., ZigBee, Bluetooth™ or Bluetooth Low Energy (BLE) or Bluetooth Smart at 2.1-2.5 GHz), or WiFi/wireless local area network (WLAN)/IEEE 802.11 standard channel frequencies (e.g., Wi-Fi 802.11 for the 2.4 GHz ISM band, or 3.6 GHz or 5 GHz WiFi bands, or White-Fi band of 479-710 MHz), among other wireless communication formats or protocols and associated operating frequencies, by way of non-limiting examples. The ambient radio frequency signals near the device 100 can be received via the antenna or antennae indicated generally at 110 in FIG. 3. The magnetic field component of the electromagnetic energy in the received signals can induce electricity in the energy harvesting and conditioning circuit 112 that can be amplified or multiplied and stored by the voltage multiplier 122 and energy storage element 124, respectively, on an ongoing basis to provide power to the other electronic components in the device 100 as needed to operate such as to receive user input (e.g., a tactile input, or smart phone NFC exchange or other input) to initiate a process, and display content (e.g., display content continuously, periodically or in response to user). Plural matching circuits 120 can be provided as interfaces between respective antennae 110 and the voltage multiplier 122 as needed depending on the different ambient radio frequency signals used to harvest energy. In addition, if ambient light energy is harvested (e.g., visible light), a photovoltaic cell can be provided to collect the energy and provide a voltage input to the voltage multiplier 122 or directly to the energy storage element 124.

With continued reference to FIGS. 1A and 1B, the device 100 is illustrated, by way of an example, as outputting static content (e.g., an advertisement about a product such as a type of pen needle used for diabetes management) in FIG. 1A and a user prompt 102 instructing a user to press the designated area 102 on the display 108 of the device 100 to play content. When a user touches the user input device 102 (e.g., a tactile sensor on the device 100 or a designated touchscreen area on the display 108), the processor 104 receives an input signal, and can be programmed to output previously stored content in response to the input signal as shown in FIG. 1B. The content can be, for example, a video segment providing more information about the pen needle that was displayed on the static content screen shown in FIG. 1A. The video segment can include audio information via the speaker 114 or not. Alternatively, the content in FIG. 1B can be different static content from that show in FIG. 1A, or series of static images.

The device 100 is configured to output a video segment or other dynamic content without a pause input option for the user; however, a pause feature can be provided via the user input 102. For example, a separate icon can be generated on an area of the display 108 to show a toggling PAUSE or PLAY icon. If the user input device 102 is separate from the display (e.g., a tactile sensor on the device 100), input signals from the user input device 102 can be processed during video output to toggle between pausing or playing the video each time the user input device 102 is activated. The device 100 can also be configured with a user input device 102 that is a motion or occupancy or proximity sensor that detects, for example, when a user is proximal to the device 100, and automatically plays the dynamic content when user proximity is sensed without the user having to touch a tactile sensor or the touchscreen display 108.

With continued reference to FIGS. 1A, 1B, 2 and 3, the processor 104 in the device 100 can be configured to respond to user input to play a dynamic content segment only once per user activation event (e.g., finger contact with at least a designated touchscreen area on the display 108 or with a user input device 102 that is separate from the touchscreen 108), or repeat play a selected number of times depending on energy used to output a video segment. For example, the device 100 can be controlled to play a video or moving images, or series of graphical content or photographs or other types of images, over a relatively short period of time (e.g., about 15 seconds) and can replay the video or series of images a selected number of times per day. The device 100 can also be controlled to no longer play the video or images after a designated time and/or date (e.g., stop playback of content after 30 days or other selected number of days or months, or during designated time periods such as outside of normal store operation hours). The processor 104 in the device 100 can also be configured to output different smaller selected portions of a video demonstration or advertisement with pauses (e.g., display of a static image) between video segments to conserve stored energy at the device 100 and depending on the rate at which ambient energy (e.g., radio frequency signals or ambient light energy at the point of user interaction) is converted by the energy harvesting and conditioning circuit 112 into voltage stored on the energy storage element 124 and the rate at which power provided by the energy storage element 124 is consumed during operation of the device. The video content can be a video segment of duration ranging, for example, between 5 seconds and 3 minutes, depending on energy requirements of the device 100 to playback the segment and the efficiency of maintaining sufficient charge on the energy storage element 124 to power the device 100 during playback. Alternatively, the processor 104 in the device 100 can be configured to output a series of static images, each displayed for a selected period of time (e.g., 1-3 seconds) before the next image in the series is automatically displayed. For example, a display 108 can be an EPD that displays and holds 10-15 images over a selected period (e.g., 15-60 seconds). Alternatively, the display 108 can be, for example, a memory LCD with embedded memory in pixel display technology (e.g., available from Sharp Electronics Corp.).

Figure 4A:
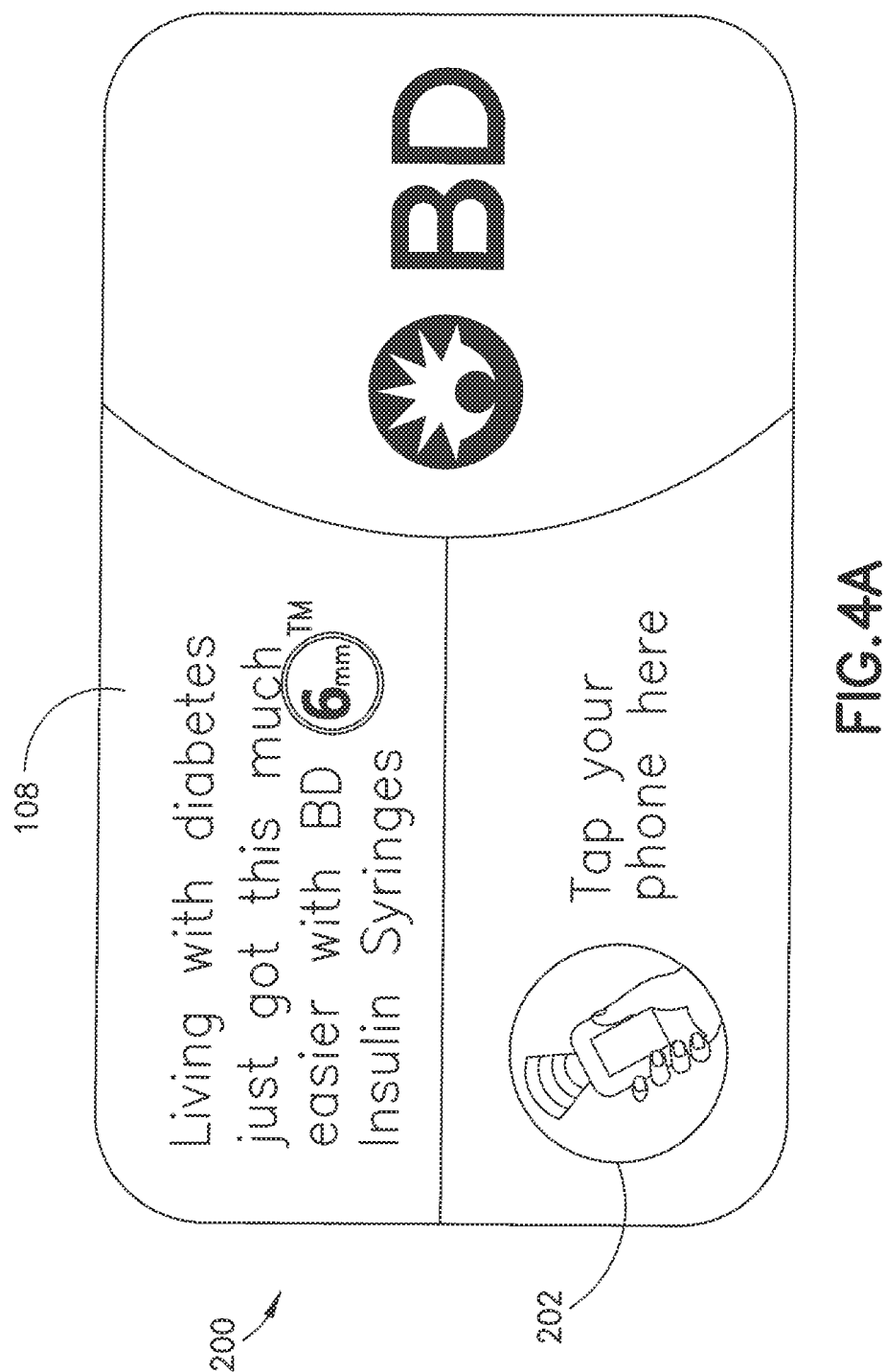
FIGS. 4A and 4B depict a self-powered, point of user interaction device that provides, respectively, viewable static and dynamic content in accordance with another embodiment of the present invention.
Figure 4B:
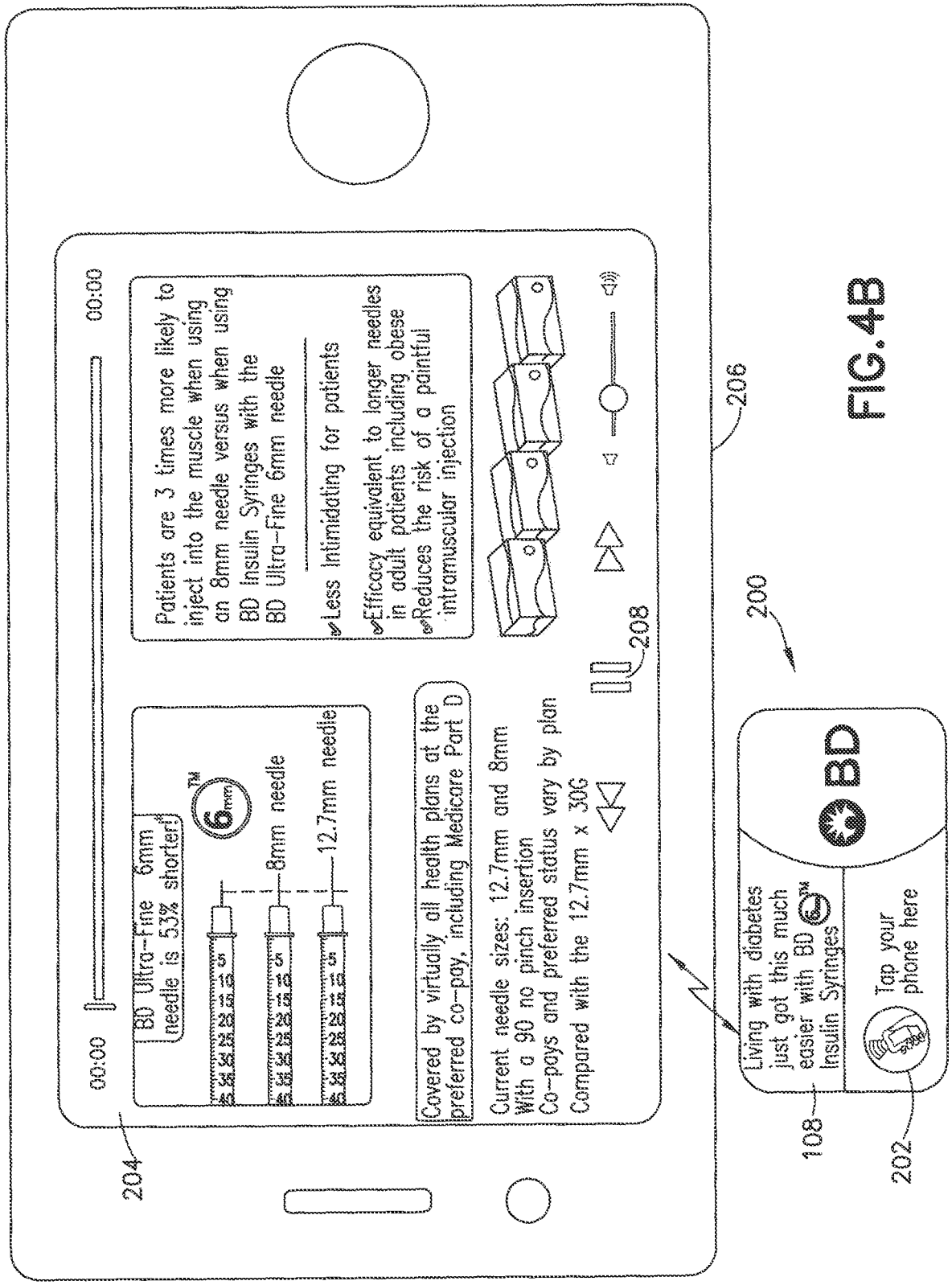

With reference to FIGS. 4A and 4B and in accordance with another embodiment of the present invention, a device 200 is provided for displaying or otherwise playing back or outputting static content (e.g., a static image generated on an LED or LCD display) via a display on the device 200 as shown in FIG. 4A, and wirelessly transmitting stored dynamic content to a smart phone or other portable computing device 206 for output via its display 204 when in a dynamic mode of operation as shown in FIG. 4B. The device 200 can be similar in size and construction as the device 100 as described above in connection with FIGS. 1A, 1B, 2 and 3. In addition, the device 200 is configured to wirelessly communicate with the smart phone or other portable computing device 206.

For example, as shown in FIG. 4A, the device 200 can display a static image. As described above in connection with the device 100, the display area shown in FIGS. 4A and 4B is essentially the total front surface area of the device 200. The device 200, however, can be configured to have a smaller display area than its viewable front surface area. The device 200 can be provided with a user input device area 202 on the viewable front surface area that can be a part of, or separate from, the display 108 provided on the device 200. For example, the display 108 of device 200 can be a LCD display capable of touchscreen input from a displayed prompt (e.g., "Tap your phone here" and corresponding icon 202). Since the device 200 operates in conjunction with a smart phone or other portable device 206 that presumably has a color LCD or LED display and touchscreen inputs or other device inputs for video viewing control operations (e.g., pause, resume, play, rewind or skip backward, and fast forward and skip forward), the display 108 on the device 200 need only output static images and can therefore be a relatively inexpensive display if desired such as an Electronic Paper Display (EPD) using E-ink technology.

With continued reference to FIGS. 4A and 4B, the device 200 can be programmed to communicate with the smart phone or other portable device 206 using a wireless communication protocol such as, for example, RFID or other near field communication (NFC) protocol or Bluetooth™ to pair or otherwise recognize the smart phone or other portable device 206 when it is brought into close proximity to the device 200 (e.g., tapping the user input 202 with a smart phone 206). In response to the device 200 acknowledging or pairing with the smart phone 206, the processor 104 in the device 200 is configured to stream selected dynamic content stored at the device 200 to the smart phone or other portable device 206 for playback on its display 204. This is advantageous since many existing smart phones and device 206 are not NFC-enabled. Such devices 206 have typically been required to have an NFC application installed on them to first energize and communicate with an RFID tag, for example, to receive merely a website link. These devices 206 would then have to navigate to a browser to use the link received from the RFID tag for playback. Proposed NFC-enabled devices 206, while more automated and requiring less user configuration, will still similarly need to download desired content from the internet to playback that content. The device 200, by contrast, advantageously directly sends desired stored content such as a video segment, or alternatively a series of static images, to the smart phone or device 206 for immediate playback on its display 204 without having to look up content on the internet.

Figure 5:
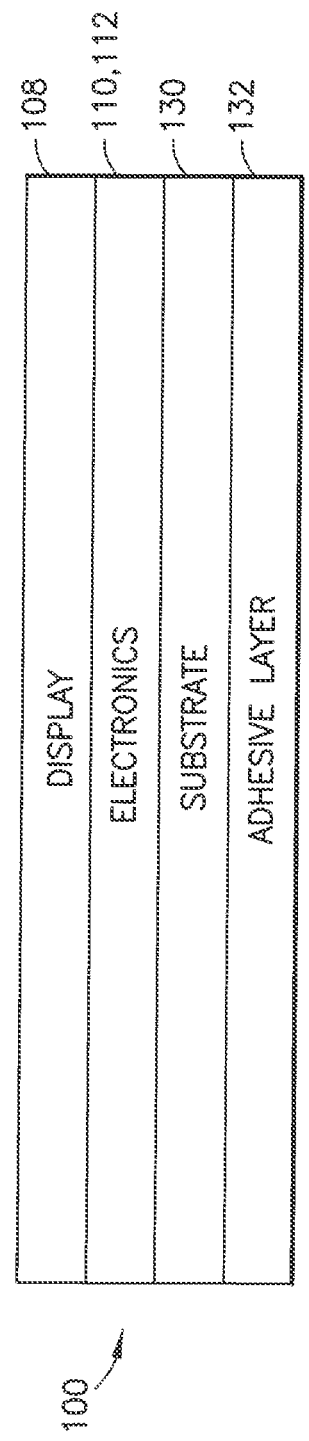
FIG. 5 depicts a cross-section of a self-powered, point of user interaction device in accordance with an embodiment of the present invention.

FIG. 5 is an illustrative cross-sectional view of the device 100 or 200. The depth or thickness of the device 100, 200 can vary depending on the construction of the device (e.g., materials used for display 108 and base) and its components (e.g., components depicted in FIG. 2). For example, the device 100, 200 can comprise multiple layers, for example, with a substrate or base layer 130 on which components such as the processor 104, memory 106, antenna 110 and energy harvesting and conditioning circuit 112 are mounted. The base 130 can be constructed from a flexible or rigid material having a display 108 that is mounted on or affixed to a surface of the base or integrally formed with the base. The display 108 can be rigid or flexible (e.g., an organic LED or OLED). The base 130 of the device 100 can be provided with an optional adhesive or magnetic or Velco™ layer 132 on one side thereof for adhering to a shelf, wall or other surface where a point of user interaction is desired. The display 108 can also have an optional protective layer (not shown) such as a protective film layer). The thickness of the device 100, 200 is preferably less than 0.5" to achieve a slim profile at the point of user interaction and less than 5"×7" in height and width to achieve a small footprint in terms of display space. For example, the device can be configured as a 2"×4" sticker or label with a thickness in the range of, for example, 0.125"-0.3", for mounting or adhering to a retail shelf.

The device 100, 200 is advantageous because it reduces field maintenance relative to conventional display devices that require battery replacement or recharging via a connection to an AC or DC power source or cumbersome and/or costly light source energy conversion components. Also, reliance on a light source for power of a display device is sometimes not feasible at points of user interaction where lighting is dim or erratic (i.e., unavailable due to lighting being dimmed or off either intentionally or unintentionally such as lack of sufficient ambient lighting). The illustrative embodiments of the present invention are advantageous because they can use ambient RF energy harvesting, which can optionally be combined with inexpensive and less cumbersome photovoltaic cell technology, for charging the energy storage element 124 using harvested ambient energy.

Further, the device 100, 200 is advantageous because, in addition to being self-reliant for power using ambient RF energy harvesting, an RF communication capability can be provided via the processor 104 and RF receiver (e.g., wireless receiver that is integrated with or separate from the energy harvesting and conditioning circuit 112) to allow mesh networking to push configuration settings and content to the devices 100, 200 in a wireless network.

The device 100, 200 is low cost and easily accessible to consumers, retail store or other commercial enterprise personnel, to healthcare professionals, pharmacists and pharmacy technicians, or any other type of person in the work force for educational and/or promotional purposes. The device 100, 200 is versatile in terms of the content and messaging that can be delivered to users at a point or user interaction. In addition to using the devices 100, 200 as shelf tags in a traditional retail environment, the devices 100, 200 can be used to deliver any type of information in just about any type of setting application. For example, a device 100, 200 can be provided on packaging for an epi-pen or defibrillator or long term care product or diabetes care device (e.g., a pump or pen or needle adapter or other injection device or blood monitoring device) or other piece of more complex healthcare equipment more commonly deployed in a hospital, laboratory or pharmacy setting, to educate the user on proper use of the product, device or equipment. Placing a device 100, 200 in proximity of, or on packaging of, equipment guides the patient, caregiver or medical care provider with real-time instructions on how to use medical equipment, and can also be used for non-medical applications. The devices 100, 200 can be implemented in various sizes on product packaging or on the products themselves to conveniently provide a combination of static and/or dynamic instructions for how to use products such as consumer products (e.g., personal care item or household appliances), office products such as photocopiers and scanners, for example, and more complex equipment such as may be employed in medical or industrial settings.

The device 100 represents a significant improvement for point of user interaction messaging since, in the past, it has been cost prohibitive for many manufacturers, retailers and suppliers and individuals to deliver a video or other dynamic demonstration of a product or an idea to individuals at the retail point of sale, in a healthcare setting/clinic, in the home, at a trade show, or any other user interaction location, without the use of a battery-operated screen, TV monitor, computer, iPad, or smart phone. For example, an in-store video promotion opportunity has in the past been too expensive for many retailers or promotors or educators to implement, since the point of purchase, promotional or educational video display required a device with a large shell or housing that is battery operated, bulky, and was too cumbersome to be used at many different points of user interaction, as well as being too cost prohibitive to produce or acquire.

Illustrative embodiments of the present invention represent an improvement over conventional point of interaction display devices since they can be produced relatively inexpensively (e.g., unit price of $5 or less such as $1-$3 per device 100, 200) and can have a significantly smaller profile and/or footprint to allow their use at many different points of user interaction. Alternatively, the devices 100 and/or 200 can employ a higher quality display that may be subject to higher unit price (e.g., greater than $5 with pricing per unit likely dependent on quantity of units, that is, reduced unit cost with greater quantities ordered). In addition, the various components and operations of the devices 100, 200 can be selected and configured to achieve a desired unit value per device 100, 200 based, for example, on the type of processing device and amount of processing power it provides, the amount of data to be displayed, the type of display (e.g., a relatively inexpensive display that produces only black and white images or is an EPD, or a more expensive color LCD or LED display), the number and types of ambient energy collecting devices used (e.g., antenna(e) 110 and matching circuit(s) 120) based largely on the amount of content to be displayed by a device 100 or transmitted from a device 200 to a smart phone, and so on.

The devices 100, 200 can be particularly important to help raise awareness and generate trial of new products and services by visually communicating, in the right place and at the right time, the benefits of using them (e.g., such as health and lifestyle benefits of a new medical product). As such, the devices 100, 200 could be an extremely helpful way to support hospital in-services or out-patient services, by attaching instructions to expensive diagnostic equipment or other medical equipment or supplies for the users (e.g., patients or caregivers) on site, and be a low cost solution to communicate complex ideas quickly and succinctly with the use of 2D sight and sound at the time information is most needed.

Packaging of a video or other dynamic content, in a small thin screen as in a device 100, or transmission of video content directly from a device 200 to a smart phone, allows on-the-spot video with or without sound at the touch of a screen or user input on the device 100, 200 by consumers, pharmacists and pharmacy technicians, healthcare professionals, business executives, educators, or anyone else. For example, a video or series of images (e.g., 15 second video) can be an effective marketing and/or educational tool regarding a new product or product for which users benefit from instructions for use and/or installation or configuration guide. This type of "video packaging" can be adhered to or otherwise mounted on an in-store display via an adhesive or magnet at the top of a clip strip, a metal gondola, on a shelf talker, in front of or behind a pharmacy counter, in a clinic, or on a pharmacy refrigerator, for example, and removed as needed to show to someone at a counseling counter or help desk and then replaced. This type of packaging of a video offers utility not offered by other information display mechanisms that are bulky and expensive. It may be housed inside another display or it could just be a stand alone 2"×4" sticker (or any other size that meets the situational need such as a 4"×6," 5"×7", or other size device 100, 200), for example, that is mounted on some other larger display vehicle or mailer. The devices 100, 200 can also be disseminated to individuals inexpensively by mail, handed out in person by other individuals (in store, in a physician's office, upon hospital discharge, in a mall, etc.), as well as worn by people, mounted on or adhered to a wall, display, or object of choice and then optionally removed and placed on something else. As stated above, the content provided by the devices 100, 200 can be reprogrammed and updated.

The components of the illustrative devices, systems and methods employed in accordance with the illustrated embodiments of the present invention can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of the invention can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The above-presented description and figures are intended by way of example only and are not intended to limit the present invention in any way except as set forth in the following claims. It is particularly noted that persons skilled in the art can readily combine the various technical aspects of the various elements of the various illustrative embodiments that have been described above in numerous other ways, all of which are considered to be within the scope of the invention.

The invention claimed is:

1. A device for playback of dynamic content at a point of user interaction comprising:
    a display;
    a memory device for storing content comprising the dynamic content;
    a processor configured to controllably output the stored content;
    an energy harvesting and conditioning circuit comprising an energy storage element and configured to receive ambient radio frequency energy available at the point of user interaction and charge an energy storage element without use of an external AC or DC power source, wherein the energy storage element is configured to supply power to the display, the memory and the processor to controllably output the stored content, and the number of repetitions of the dynamic content playback is determined based on an amount of power charged in the energy storage element by the ambient energy collecting and storage device, and an amount of power consumed by display of the dynamic content; and
    a substrate on which the display, the memory device, the processor and the energy harvesting and conditioning circuit are mounted, the substrate having a top side from which the display is viewable by a user and a bottom side for mounting the substrate at the point of user interaction;

wherein the device is self-reliant for power using only ambient radio frequency energy harvested via the energy harvesting and conditioning circuit; and wherein the dynamic content is video content comprising video segments and the processor is configured to output them with pauses and a display of a static image between video segments to conserve stored energy at the device and depending on the rate at which ambient energy is converted by the energy harvesting and conditioning circuit and the rate at which power provided by the energy storage element is consumed during playback.

2. The device of claim 1, wherein the substrate has dimensions comprising a height in the range of 2"-5" and a length in the range of 4"-7".

3. The device of claim 1, wherein the substrate has dimensions comprising a thickness in the range of 0.125"-0.5".

4. The device of claim 1, wherein the dynamic content is a video segment.

5. The device of claim 4, wherein the video segment has a duration in the range of 5 seconds-180 seconds.

6. The device of claim 1, wherein the processor is configured to playback the dynamic content via the display automatically in response to a user input.

7. The device of claim 5, wherein the device comprises a user input device selected from the group consisting of a tactile switch, a touchscreen area on the display, a user proximity sensor.

8. The device of claim 5, wherein the processor plays the dynamic content one time per user input.

9. The device of claim 6, wherein the processor plays the dynamic content continuously in a loop.

10. The device of claim 6, wherein the processor plays the dynamic content periodically.

11. The device of claim 1, wherein the memory device stores static content, and the processor is configured to display the static content until a user input signal is received and then output the dynamic content in response to the user input signal.

12. The device of claim 11, wherein the user input signal is received from a user-activated input device selected from the group consisting a tactile switch, a touchscreen area on the display, and a user proximity sensor.

13. The device of claim 11, wherein the processor is configured to transmit the stored dynamic content to a proximal smart mobile device in response to a user input for playback on a display of the smart mobile device.

14. The device of claim 13, wherein the smart mobile device is near field communication or NFC-enabled and the device further comprises a near field communication circuit and the user input is a user bringing the smart mobile device into proximity with the near field communication circuit of the device, and the processor is configured to transmit the stored dynamic content to the smart mobile device via the near field communication circuit when the near field communication circuit is activated by proximity of the smart mobile device.

15. The device of claim 1, wherein the dynamic content is displayed as a series of successive images.

16. The device of claim 1, wherein the ambient radio frequency energy is ambient wireless network energy and the energy harvesting and conditioning circuit comprises at least one antenna configured to receive ambient radio frequency signals, a matching circuit, a voltage multiplier and an energy storage element.

17. The device of claim 1, wherein the ambient radio frequency energy is ambient light energy and the energy harvesting and conditioning circuit comprises a photovoltaic cell configured to collect ambient light energy and produce a corresponding voltage input to a voltage multiplier connected to an energy storage element, or directly to the energy storage element.

18. The device of claim 1, wherein the bottom side of the substrate is mounted at the point of user interaction using a selected one of a mounting bracket, or a clip strip on a display shelf, or a Velcro fastener, or applied directly to packaging, or applied directly to a wearable item.

19. The device of claim 1, wherein the stored content comprises static content and dynamic content, and the processor is configured to operate in a static mode and a dynamic mode, the processor outputting the static content via the display when in the static mode and then operating in the dynamic mode to output the dynamic content via the display in response to a user input.

20. The device of claim 1, wherein the display is chosen from a light emitting diode (LED) display and a liquid crystal display (LCD).

\* \* \* \* \*